United States Patent
Payne (10) Patent No.: US 9,983,184 B2
(45) Date of Patent: May 29, 2018

(54) USING FLUORESCENCE MEASUREMENTS FOR CHARACTERIZING PROTEIN GEL-FIRMING PROCESSES

(71) Applicant: Reflectronics, Inc., Lexington, KY (US)

(72) Inventor: Fred Payne, Lexington, KY (US)

(73) Assignee: REFLECTONICS, INC., Lexington, KY (US)

( * ) Notice: Subject to any disclaimer, the term of this patent is extended or adjusted under 35 U.S.C. 154(b) by 867 days.

(21) Appl. No.: 14/491,537

(22) Filed: Sep. 19, 2014

(65) Prior Publication Data

US 2015/0088472 A1   Mar. 26, 2015

Related U.S. Application Data

(60) Provisional application No. 61/880,224, filed on Sep. 20, 2013, provisional application No. 61/930,080, filed on Jan. 22, 2014.

(51) Int. Cl.
 G01N 33/48   (2006.01)
 G01N 33/04   (2006.01)

(52) U.S. Cl.
 CPC .................. G01N 33/04 (2013.01)

(58) Field of Classification Search
 None
 See application file for complete search history.

(56) References Cited

U.S. PATENT DOCUMENTS

| | | |
|---|---|---|
| 5,172,193 A | 12/1992 | Payne et al. |
| 5,288,642 A | 2/1994 | Turner |
| 5,399,866 A | 3/1995 | Feldman et al. |
| 5,798,221 A | 8/1998 | AEgidius |
| 5,863,401 A | 1/1999 | Chen |
| 5,972,641 A | 10/1999 | Ofjord et al. |
| 5,978,435 A | 11/1999 | Christensen et al. |
| 6,165,742 A | 12/2000 | Ofjord et al. |
| 6,413,779 B1 | 7/2002 | Birlouez-Aragon |
| 6,511,819 B2 | 1/2003 | Tryland et al. |
| 7,172,872 B1 | 2/2007 | Eckersall et al. |
| 7,288,767 B2 | 10/2007 | Ridder |
| 7,312,073 B2 | 12/2007 | Shaw et al. |
| 7,374,900 B2 | 5/2008 | Soukharev et al. |
| 7,432,978 B2 | 10/2008 | Storm |
| 7,556,932 B2 | 7/2009 | Cheng et al. |
| 7,880,881 B2 | 2/2011 | Everard et al. |
| 8,010,299 B2 | 8/2011 | Arnivardson |

(Continued)

OTHER PUBLICATIONS

C. C. Fagan, et al.; "Preliminary evaluation of endogenous milk fluorophores as tracer molecules for curd syneresis"; Journal of Dairy Science (2011), vol. 9, No. 11, pp. 5350-5358.

(Continued)

Primary Examiner — Larry D Riggs, II
(74) Attorney, Agent, or Firm — King & Schickli, PLLC (57) ABSTRACT

The present invention relates to a method of predicting the cutting-time of coagulating milk based upon time parameters generated from fluorescence measurements. The method includes the steps of (a) measuring a change in the fluorescence response of coagulating milk, (b) generating time parameters from the fluorescence response, and (c) using time parameters and a cutting time prediction equation to predict cutting time. Additionally, an additional method is provided for determining a cutting time prediction equation by regression analysis.

20 Claims, 7 Drawing Sheets

(56) References Cited

U.S. PATENT DOCUMENTS

| | | |
|---|---|---|
| 8,072,596 B2 | 12/2011 | Katz et al. |
| 8,154,731 B2 | 4/2012 | Arnivardson et al. |
| 2010/0282982 A1 | 11/2010 | Schrieber et al. |
| 2012/0252694 A1 | 10/2012 | Zhang et al. |

OTHER PUBLICATIONS

C. Blecker, et al.; "Effect of heat treatment of rennet skim milk induced coagulation on the rheological properties and molecular structure determined by synchronous fluorescence spectroscopy and turbiscan"; Food Chemistry (2012), vol. 135, pp. 1809-1817.

USING FLUORESCENCE MEASUREMENTS FOR CHARACTERIZING PROTEIN GEL-FIRMING PROCESSES

This utility patent application claims the benefit of priority in U.S. Provisional Patent Application Ser. No. 61/880,224 filed on Sep. 20, 2013, and U.S. Provisional Patent Application Ser. No. 61/930,080, filed on Jan. 22, 2014, the entirety of the disclosures of which are incorporated herein by reference.

TECHNICAL FIELD

The present invention relates generally to a method for accurately predicting the endpoint of an enzymatic milk coagulation process and, more particularly, to a method of predicting the cutting time of a milk coagulum based upon time parameters generated from fluorescence and infrared light backscatter measurements.

BACKGROUND

The first major step in the cheese making process is the coagulation of milk by enzymatic hydrolysis of K-casein. The hydrolysis of K-casein leads to destabilization of the colloidal system of the milk. This is followed by aggregation of the micelles into clusters. Over time, the clusters grow in size. This growth in size is followed by crosslinking between chains which eventually transform the milk into a gel or coagulum. Once a desired point is reached in the coagulation process, the coagulum is "cut," e.g., by traversing with knives to slice the coagulum into small pieces.

Selection of the optimum point to cut the coagulum has been a subject of much research. It has been shown that coagulum strength at cutting effects the recovery of milk components during cheese making. More particularly, milk components not entrapped in the K-casein matrix are lost into the whey. Thus, cutting the coagulum when extremely soft decreases cheese yield due to the increased loss of fat and curd fines. Conversely, cutting when the coagulum is too firm retards syneresis and results in high moisture cheese. Further, it has also been suggested that coagulum strength affects the quality of the returning cheese.

Curd firmness and the rate of firming are affected by many factors. For example, high K-casein concentration increases curd firmness. The time and temperature of milk storage prior to cheese manufacture also affects curd firmness. Homogenization and standardization may also influence curd firmness. Other factors affecting firmness are the breed of the cow from which milk is collected, period of lactation of the cow, milk quality, and type of enzyme used in cheese making.

Cheese makers typically schedule cutting of the coagulum 25 to 30 minutes after adding the enzyme, however the coagulum may not have a consistent strength due to many factors. Many systems have been proposed for determining cutting time.

For example, U.S. Pat. No. 5,172,193, incorporated herein by reference, discloses a method (including a mathematical algorithm or equation) for predicting the cutting time of a milk coagulum based upon the light backscatter measurements (at 880 nm). Generally, this light backscatter technology is known to provide accurate results when the milk has consistent coagulating properties. In modern dairy plants several protein sources having different enzyme reactivity are being combined as the substrate for cheese making with the effect being that the coagulating properties vary significantly, and the light backscatter technology needs frequent recalibrations to provide accurate cutting time predictions. Frequent recalibrations are not feasible in modern dairy plants. Furthermore, the methods disclosed therein require knowledge of the time the enzyme is added to the milk. In a laboratory setting, this is not per se problematic; in industrial application, however, the piping distance between the enzyme supply and the cheese making vat may vary, making the exact determination of the reference time a significant challenge.

More recently, cheese making plants have begun increasing the protein content of the milk by adding dried skim milk solids or removing some of the liquid from milk by ultrafiltration while others have begun decreasing the milk pH (some by using carbon dioxide injection into the milk) to increase the enzymatic reaction rates and produce products with improved functional characteristics. These new and existing challenges have impaired the ability of the previously known methods to provide accurate cutting time predictions over a broader range of protein substrates having different enzymatic reactivities. Accordingly, there is a need in the art for improved devices and methods for accurately predicting the cutting time of a milk coagulum under more variable processing conditions and methods.

SUMMARY

In accordance with the purposes described herein, a method is provided for generating and using time parameters from one or more optical responses for use in predicting the cutting time of a milk coagulum. The method may be broadly described as including the steps of: (a) measuring the fluorescence response change of the milk coagulum; (b) generating a time parameter from the fluorescence response change; and (c) using the time parameter and a cutting time prediction equation to predict the cutting time of the milk coagulum. Additionally, in some embodiments, the method may include a light backscatter response change and/or multiple time parameters.

In one embodiment, the method includes normalizing the fluorescence response change by taking the average of a measured fluorescence response for the first minute after a time zero; time zero simply refers to the time, or midpoint of time period, when the enzyme is added to the milk to initiate enzymatic coagulation.

In one embodiment, the method includes generating a time parameter from the fluorescence response change by using a derivative thereof.

In one embodiment, the method includes generating the time parameter from multiple derivatives of said fluorescence response change.

In accordance with an additional aspect, a method is provided for deriving a cutting time prediction equation of a milk coagulum. The method may broadly be described as: (a) developing a coagulation profile of milk using a fluorescence response change of a compound within said milk coagulum, (b) analyzing the coagulation profile to determine time parameters, and (c) deriving the cutting time prediction equation using the time parameters.

In one embodiment, the method includes determining the cutting time prediction equation using regression analysis.

In one embodiment, the method includes the additional step of predicting the cutting time of a milk coagulum.

In one embodiment, the cutting time prediction equation is dependent upon a time delay.

In one embodiment, the cutting time prediction equation is dependent upon product characteristic of the coagulating milk. Product characteristics generally include fat, protein, solids content, sugar content, pH, temperature, enzyme type, and combinations thereof.

BRIEF DESCRIPTION OF THE DRAWINGS

The accompanying drawings incorporated herein and forming a part of the specification, illustrate several aspects of the present invention and together with the description serve to explain certain principles of the invention. In the drawings.

Reference will now be made in detail to the present preferred embodiment of the invention, examples of which are illustrated in the accompanying drawings.

DETAILED DESCRIPTION

Prior to enzymatic coagulation of a milk sample, the milk sample is generally pasteurized, cooled to a temperature (around 31 degrees Celsius), and pumped into a cheese vat. Coagulation begins at the point in time when an enzyme is added to the milk. In large cheese making vats, the enzyme is generally diluted with water and added to the milk over a period of approximately two minutes (continual process). An alternative method of adding enzyme is a batch process where the enzyme is added to the milk all at once. Accordingly, time zero which defines the process time when enzyme is added to the vat of milk is easily defined as either (A) the midpoint in the interval over which enzyme is added to the milk (continual process) or (B) the exact time at which the enzyme is added to the milk (batch process).

Light Backscatter

Figure 1:
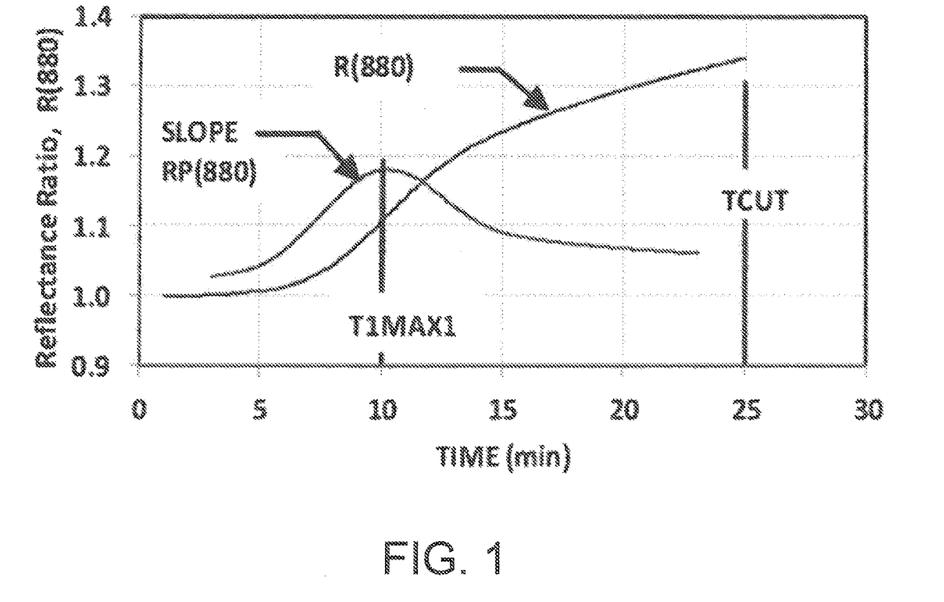
FIG. 1 illustrates a typical infrared light backscatter profile, R(880), with the calculated first derivative (slope) and the time parameter T1MAX1. R(880) is the reflectance ratio calculated by taking the ratio of the measured response at any process time to the measured response averaged over first minute of process and it is based backscatter of light from an 880 nm LED.

The three phases of the enzymatic coagulation of the milk sample have been capable of identification using infrared (880 nm) light backscatter measured during the coagulation process (see, e.g., U.S. Pat. No. 5,172,193). Reference is now made to FIG. 1 (Prior Art), illustrating a typical infrared light backscatter profile of a coagulating milk sample. As shown, the light backscatter profile has been normalized for convenience of illustration. Normalization is executed by taking the average of the measured optical responses (i.e. initial response voltages) for the first minute after time zero. Subsequent voltages are then divided by the average initial response voltage to give the light backscatter response ratio, R(880).

The slope or first derivative of the light backscatter response, R(880), is calculated with the time parameter (T1MAX1) selected as the time when the maximum slope occurs. The time parameter is generated by calculating the slope over a data segment including the most recent data points. Next, a cutting time prediction equation is used with the determined time parameter to predict a cutting time of the coagulum. Two typical cutting time prediction equations are represented below:

$$CT = \beta \times T1MAX1 \times (\text{protein function}); \text{ and}$$

$$CT = \beta \times T1MAX1$$

where CT is the cutting-time and $\beta$ is a calibration constant determined in a cheese plant. A typical value for $\beta$ is 2.0.

Both equations, however, contain significant limitations, namely, the reliance on the calibration constant, $\beta$, which itself is dependent upon coagulation properties and/or time zero. To overcome these limitations, and in accordance with the other purposes described herein, a method is provided for generating time parameters closer to the endpoint and simpler cutting time prediction equations independent of time zero. The method may be broadly described as including the steps of: (a) measuring the fluorescence response change (and optionally the infrared light backscatter response change) during the milk coagulation step; (b) generating time parameters from the fluorescence response (and optionally from the infrared light backscatter response change); and, using the time parameters from the fluorescence response with a cutting time prediction equation that is independent of time zero to predict the cutting time of the coagulum.

Additionally, a method is provided for deriving a cutting time prediction equation.

Front Face Fluorescence Measurement Configuration

Figure 3:
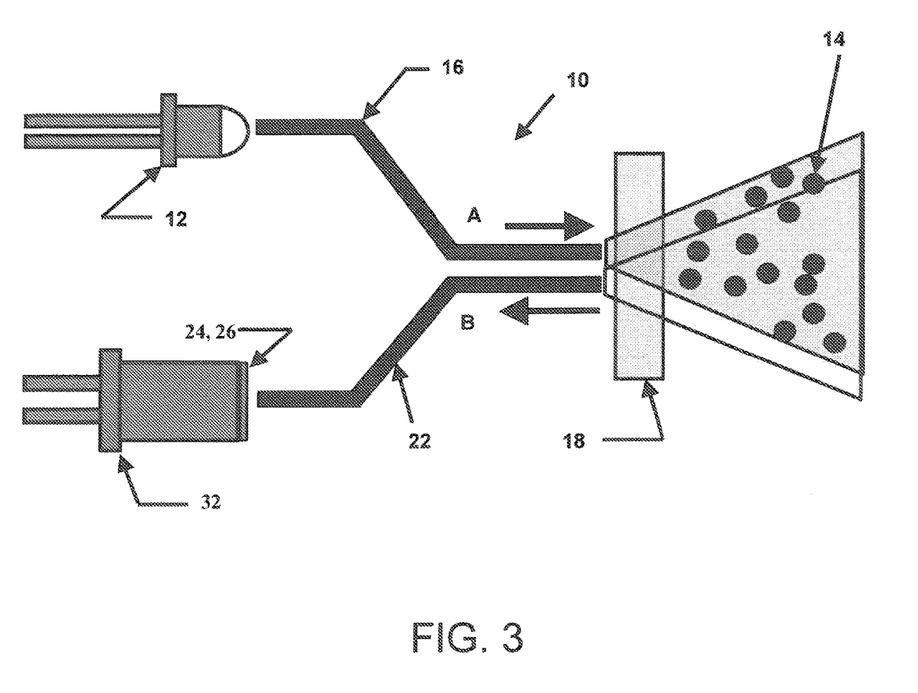
FIG. 3 illustrates an optical configuration of a front face fluorescence sensor.

Reference is now made to FIG. 3, illustrating an optical configuration of a front face fluorescence sensor for measuring a change in the fluorescence response of the coagulating milk. The front face fluorescence sensor (10) includes an ultraviolet light emitting source (12) (i.e. a light emitting diode) with a peak intensity at about 280 nm for directing ultraviolet light towards a coagulating milk sample (14) in a cheese vat (not shown) via a first optical fiber (16) (action arrow A). A sapphire window (18) is located between the first optical fiber (16) and the coagulating milk sample (14). Because the coagulating milk sample (14) contains tryptophan and riboflavin as well as other fluorescent chemical compounds, the ultraviolet light induces a fluorescence response (not shown) within the coagulating milk sample (14). A second optical fiber (22) collects the fluorescence response and any excitation light and directs it towards a series of filters (24, 26) (action arrow B).

The series of filters (24, 26) includes a low-pass filter (24) for removing the fluorescence response above a first predetermined wavelength before the fluorescence response reaches a photodetector (28). The series of filters (24, 26) further includes a high-pass filter (26) for removing the residual excitation light (or backscatter) below a second predetermined wavelength, such as about 300 to about 325 nm to remove residual excitation light. Thus, the inclusion of the series of filters allows the sensor (10) to create a waveband (not shown) containing the fluorescence response of primarily tryptophan.

Figure 2:
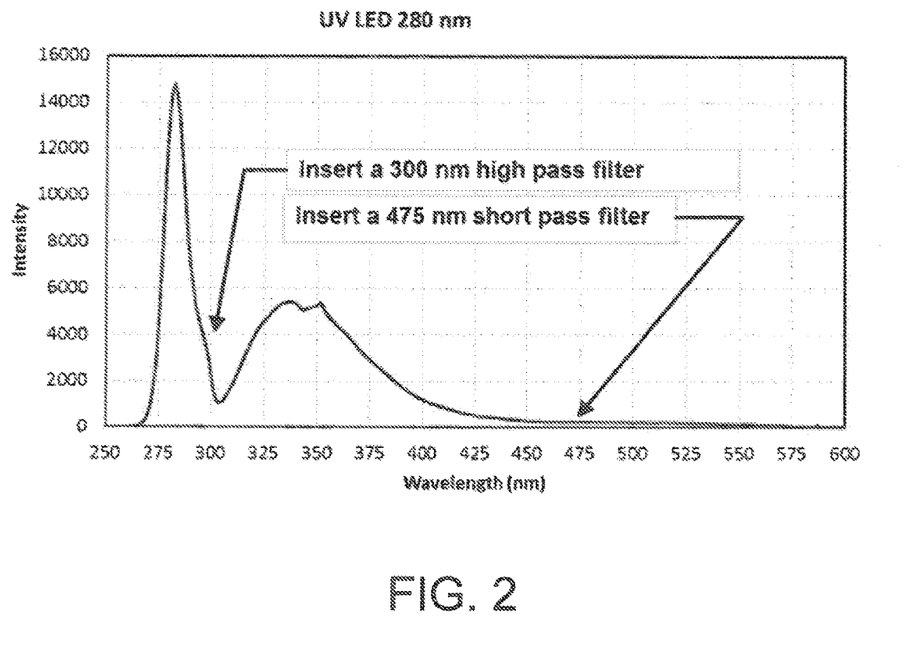
FIG. 2 illustrates the optical front face fluorescence response (including both the excitation and emission wavelengths) of milk as measured by a spectrometer.

Reference is now made to FIG. 2, illustrating the fluorescence response of a milk sample combined with the excitation light measured by a spectrometer. As shown, when the measurement of primarily tryptophan fluorescence is preferred, the preferred waveband should be centered at, or near, 350 nm. To achieve this, the first predetermined wavelength should be set at or near 475 nm, effectively filtering out any undesirable riboflavin fluorescence and the second set at 300 to about 325 nm to remove residual excitation light.

After the fluorescence response is filtered by the series of filters (24, 26), a photodetector (32) measures the fluorescence response. The response is collected for analysis, processing, and/or storage.

Use of Front Face Fluorescence Apparatus

In use, the fluorescence sensor (10) begins collecting measurements or data points of the fluorescence at a reference time, such as at time zero, and at regularly selected intervals (i.e. intervals of 1, 2, and/or 6 seconds) thereafter. Normalization of the measurements is simultaneously performed by an analyzer and/or processor for the convenience of developing a coagulation profile (i.e. a graph). Normalization is executed by taking the average of the measured fluorescence (20), or initial response voltages, for the first minute after time zero. Subsequent response voltages are then divided by the initial response voltages to give normalized fluorescence response ratios. Once normalized, the measurements are analyzed by the processor to create, develop, and/or output a coagulation profile.

Coagulation profiles by themselves are not per se useful in predicting the cutting-time of coagulating milk but are used to generate time parameters. Time parameters are generated from a derivative, or derivatives, of the normalized fluorescence response (F(350)) by calculating the slope over a selected data segment. Subsequently, the time parameters can be used in deriving a process control algorithm or cutting time prediction equation which predicts cutting time of the coagulum. This may be done, for example, by use of regression analysis as should be understood by one of ordinary skill in the art.

Example #1

The fluorescent response, F(350), was measured during the enzymatic coagulation of milk to determine if it offered an advantage over the infrared light backscatter sensor R(880). A test was conducted by adding an enzyme to pasteurized skim milk at a temperature of 31° C. Three levels of enzyme concentration were used: 0.081, 0.123 and 0.162 mg/kg for levels 1, 1.5 and 2, respectively. Both the fluorescence F(350) and infrared light backscatter R(880) responses were measured and recorded during the coagulation process. Both R(880) and F(350) are signal ratios generated by dividing the signal response by the initial signal response averaged over the first minute of the process.

Figure 4:
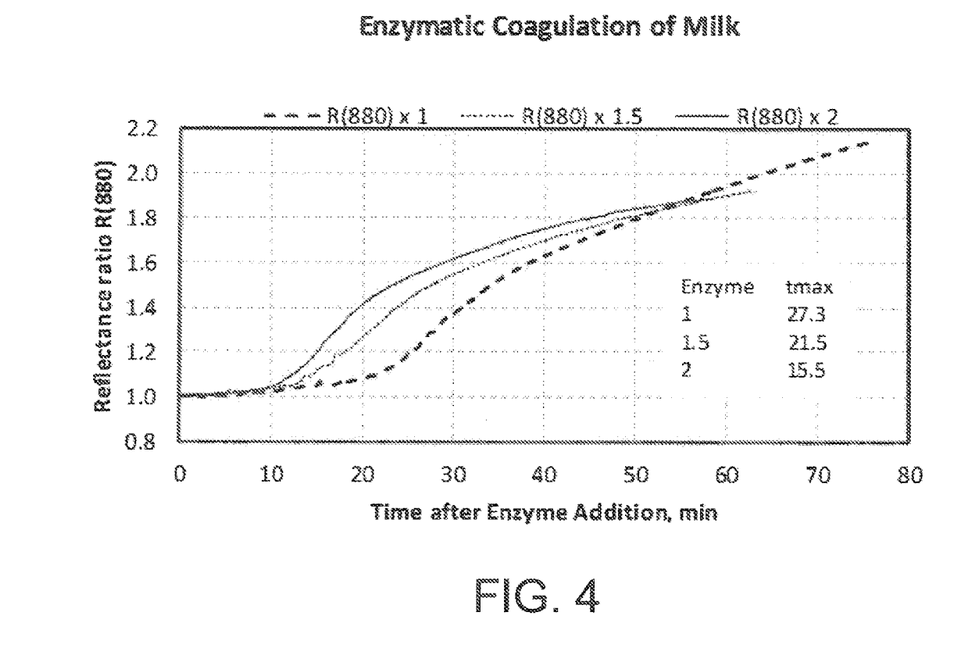
FIG. 4 illustrates the infrared light backscatter profile of coagulating milk for three enzyme concentrations.
Figure 5:
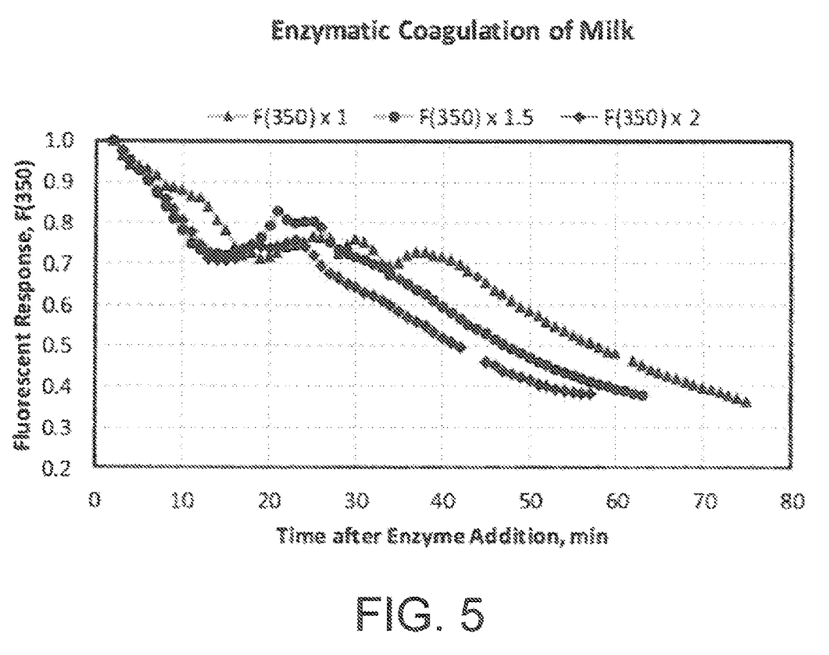
FIG. 5 illustrates the fluorescence response profile of coagulating milk for three enzyme concentrations.

Reference is now made to FIGS. 4 and 5, illustrating the light backscatter profile R(880) and the fluorescent response F(350) for the same tests (respectively).

The fluorescent response as shown in FIG. 5 has three phases. The first phase shows a signal decrease from 1.0 at time zero to approximately 0.7 at a time of about 15 minutes. The second phase consists of a wavering of the response between about 0.7 and 0.8. This wavering seems to be consistently unpredictable. The third phase (gel firming) starts when the fluorescence takes a significant drop that approaches a near constant drop rate.

Since the temperature for all three tests was the same at 31° C. it was expect the gel-firming reactions would proceed at a similar rate. This is shown in FIG. 5 by the near parallel fluorescent responses during the gel-firming phase for each test.

Figure 6:
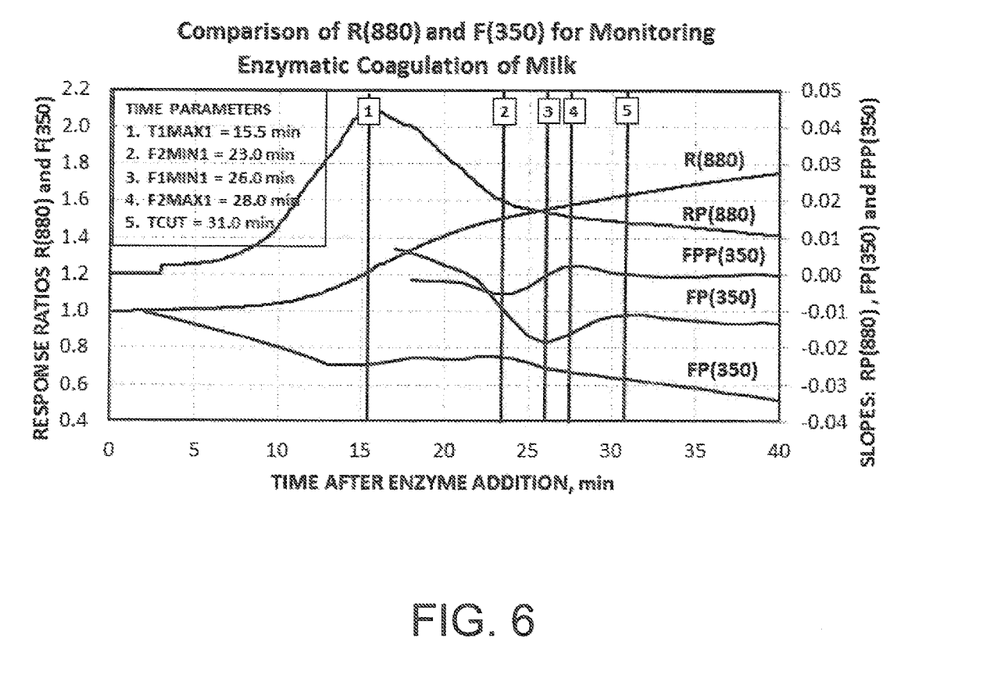
FIG. 6 illustrates milk coagulation profiles for infrared light backscatter ratio (R) and its first derivative (RP) and the fluorescence response ratio (F) and it first (FP) and second (FPP) derivatives with selected time parameters identified.

FIG. 6 shows the plot of the light backscatter profile R(880) and the fluorescence profile F(350) during the milk coagulation test for enzyme concentration level 2 along with the first derivatives RP(880) and FP(350). The endpoint or TCUT was determined subjectively by an expert cheese maker to be 31.0 minutes. The advantage of the fluorescence signal F(350) over the infrared R(880) is illustrated in FIG. 6. The time parameter T1MAX1, defined as the time when the slope of the infrared light backscatter reflectance curve R(880) reaches a maximum, occurred at 15.5 minutes after enzyme addition. The former patented technology used this time parameter to predict the endpoint. A typical prediction algorithm was TCUT=BETA*T1MAX1 where BETA=2. Thus the predicted cutting time for this test would be 31.0 minutes. Using the fluorescence sensor the time parameter F1MIN1 determined during the gel-firming phase was 26.0 min. This time event is only 5 minutes away from the TCUT of 31.0 min. It should be obvious that F1MIN1 is a much better parameter for predicting cutting time because it was determined during the gel firming stage and its occurrence is much closer to the cutting time. There is also an operational benefit. The previous technology required knowledge of the enzyme addition time or "time zero" discussed above. Knowledge of the time zero is much less important for predicting the endpoint using F1MIN1. In fact, cutting time prediction equations based solely on parameters generated within the gel firming phase from F(350) are possible. These simplified prediction equations would totally eliminate the need for time zero. Time parameters based on the second and third derivatives may also provide useful information for predicting endpoint.

Example #2

Reference is again made to FIG. 6, illustrating a comparison of light backscatter and front face fluorescence measurement responses of a coagulating milk sample. Time parameters are generated from the first and second derivatives of R(880) and F(350) by taking a selected number of the most recent data points and calculating the slope of the data segment. Typical data segments range from 1 to 8 minutes and typically 3 to 4 minutes. The derivative curves are smoothed by using larger data segments making determination of the time parameters easier to determine.

FIG. 6 shows the first derivatives RP(880) and FP(350) as well as the second derivative FPP(350). The time parameters determined from these derivative calculations are: T1MAX1, F2MIN1, F1MIN1, and F2MAX1. The endpoint of the coagulation process is referred to as the cutting time, TCUT.

It is observed that the time parameter, T1MAX1, from the infrared light backscatter sensor is 15.5 minutes and the endpoint determined by an expert cheese maker, TCUT is 31.0 minutes. The previous technology patented in 1992 correlated T1MAX1 to TCUT and a simple equation TCUT=BETA*TCUT was possible with BETA approximately 2.0. Thus it is observed that a 1.0 minute error in the determination of T1MAX1 would result in an error of 2.0 minutes in the predicted value of TCUT.

The time parameters derived from the fluorescent sensor are F2MIN1=23.0 min, F1MIN1=26.0 min, F2MAX1=28.0 min. These time parameters are much closer to TCUT than T1MAX1. In fact, F2MAX1 occurred only 3 minutes before TCUT. This is the advantage of the fluorescent technology. The time parameters are derived within the gel firming process which is the last phase of the milk coagulation process. The time parameters are much closer to the endpoint thus allowing greater precision in endpoint prediction.

The determination of a "cutting time prediction equation" must be accomplished to utilize the technology. The simplest equation is just the addition of a "time delay" to the time parameter F2MAX1. Thus, the simplest cutting time prediction equation is as follows:

$$TCUT = F2MAX1 + 3 \text{ min} \qquad \text{Equation 1}$$

Where F2MAX1 is determined from the normalized fluorescent profile and the "time delay" of 3.0 minutes is determined in the cheese plant by regression analysis of the observed cutting time OTCUT as a function of F2MAX1 or by experience of the cheese maker. The advantage of this simple equation is that the cheese maker can easily calibrate the prediction and change the time delay. The time delay has a physical meaning and is easily understood by cheese plant personnel. The second advantage is the elimination of the need to determine "time zero". The predicted cutting time TCUT does not depend on an accurate measurement of "time zero" but rather a time delay after the occurrence of a time parameter F2MAX1.

More complicated cutting time prediction equations may be generated by regression analysis of the data to cover varying conditions in the cheese making process. The following is an example:

$$TCUT = B1*(F2MAX1 - F2MIN1) + B2*PROTEIN + C \qquad \text{Equation 2}$$

Equation 2 does not rely on an accurate measure of "time zero", determines a prediction using the difference between two time parameters determined from measured fluorescence response, adjusts the prediction for protein content of milk, and includes a "time delay", C, to assist the operator in tweaking the prediction.

Some of the cheeses making plants mix different milk ingredients having different enzymatic reactivity. This has resulted in the need to frequently change BETA when using the infrared light backscatter technology because the time parameter T1MAX1 is a direct measure of enzymatic reactivity (Tabayehnejad, N., Castillo, M. and Payne, F. A. 2012, *Comparison of total milk-clotting activity measurement precision using the Berridge clotting time method and a proposed optical method*, Journal of Food Engineering 108 (2012) 549-556.). The advantage of the fluorescent technology is that the time parameters F2MIN1, F1MIN1, and F2MAX1 are so close to the process endpoint that correlations will be strong.

Clearly, a multitude of parameters could be included in the cutting time prediction equation including processing conditions and milk product characteristics (fat, protein, milk solids, milk treatment; pH, temperature, enzyme type, etc.) along with time parameters from the fluorescent sensor F2MIN1, F1MIN1, F2MAX1 and possibly in combination with time parameters from the infrared light backscatter sensor such as T1MAX1. Determination of a cutting time prediction equation for a complicated process would require data from batches covering the processing conditions normally encountered. This is easily accomplished by setting up a data collection system in the plant to collect this data over a period of time followed by multiple linear and/or non-linear regression techniques to determine the significant parameters.

The above discoveries make fluorescent monitoring of milk coagulation a very rich method for monitoring the gel-firming reactions as well as developing a method for predicting a desired endpoint (cutting time). The ability to use F(350) to monitor gel firming in the enzymatic coagulation of milk for cheese making has great potential for more precisely predicting an endpoint (cutting time) and with a simpler and easier-to-implement cutting time prediction equation.

Figure 7:
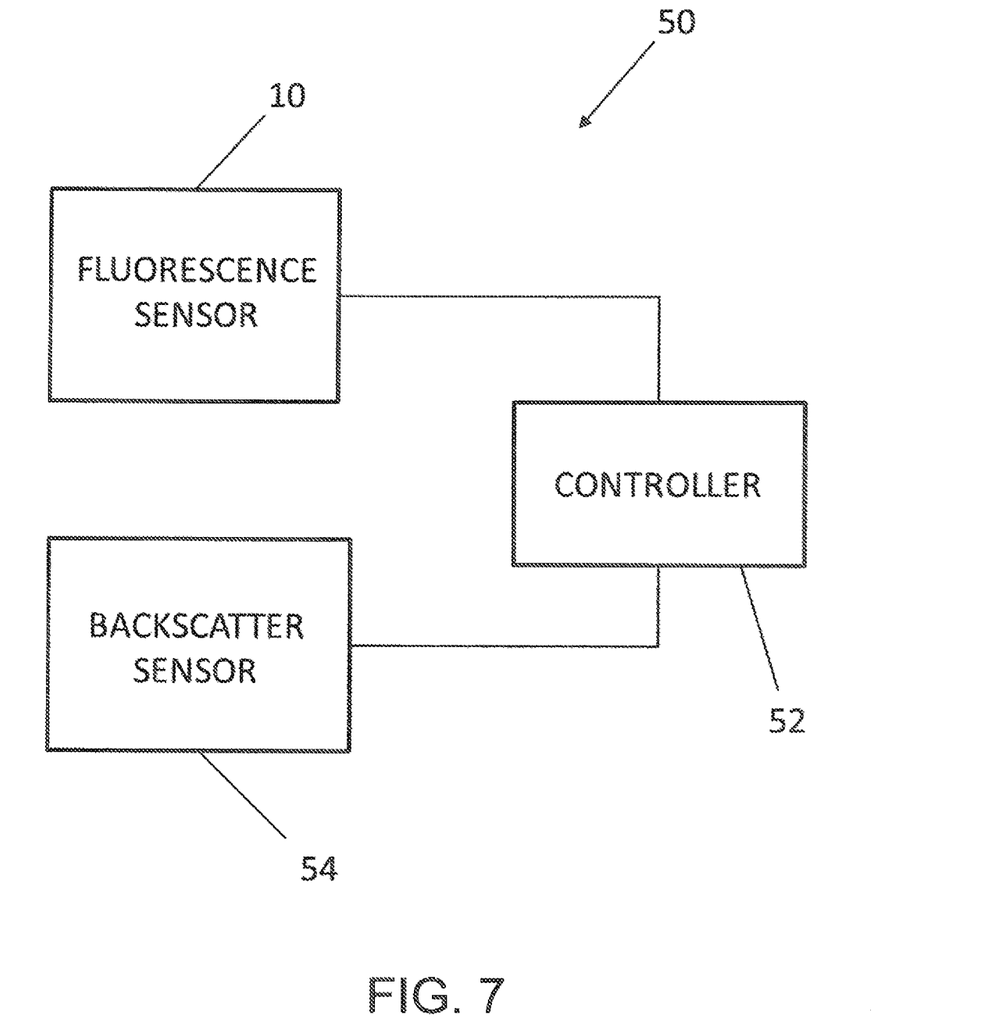
FIG. 7 is a schematic block diagram of one possible apparatus used to complete the method.

In summary, a method is provided for generating and using time parameters to predict the cutting time of a milk coagulum by means of an apparatus 50 including (a) a controller 52, in the form of a computing device such as a dedicated microprocessor, (b) a fluorescence sensor 10 and (c) a backscatter sensor 54 such as described in U.S. Pat. No. 5,172,193. That method may be broadly described as measuring, with a fluorescence sensor 10, a fluorescence response change of the milk coagulum, generating, by a controller 52, a first time parameter from the fluorescence response change and predicting, by the controller, the cutting time of the milk coagulum based upon the first time parameter and a predetermined cutting time prediction equation.

In still another embodiment, the method also includes measuring, by a backscatter sensor 54, a light backscatter response change of the milk coagulum, generating, by the controller 52, a second time parameter from the light backscatter response change and using by the controller, the first and second time parameters and a second predetermined cutting time prediction equation to predict the cutting time of the milk coagulum.

The foregoing has been presented for purposes of illustration and description. It is not intended to be exhaustive or to limit the embodiments to the precise form disclosed. Obvious modifications and variations are possible in light of the above teachings. All such modifications and variations are within the scope of the appended claims when interpreted in accordance with the breadth to which they are fairly, legally and equitably entitled.

I claim:

1. A method of generating and using time parameters to predict the cutting time of a milk coagulum comprising:
   (a) applying ultraviolet light with a peak intensity of about 280 nm to the milk coagulum from an ultraviolet light emitting diode source;
   (b) detecting light reflected from the milk coagulum in (a) with a fluorescence sensor, wherein detected light passes through both a high pass filter to remove light below 300 nm and a low pass filter to remove light above 475 nm;
   (c) measuring, by the fluorescence sensor, a fluorescence response change of said milk coagulum;
   (d) generating, by said controller, a first time parameter from said fluorescence response change; and
   (e) using, by said controller, said first time parameter and a cutting time prediction equation to predict the cutting time of said milk coagulum.

2. The method of claim 1, further comprising:
   measuring, by backscatter sensor, a light backscatter response change of said milk coagulum;
   generating, by said controller, a second time parameter from said light backscatter response change; and using, by said controller, said first and second time parameters and a second cutting time prediction equation to predict the cutting time of said milk coagulum.

3. The method of claim 1, wherein said fluorescence response change is normalized by taking the average of said fluorescence response change for a first minute after a reference time.

4. The method of claim 3, wherein said reference time is the time at which an enzyme is added to said milk coagulum.

5. The method of claim 1, wherein said generating includes using a derivative of said fluorescence response change.

6. The method of claim 5, wherein said generating further includes using multiple derivatives of said fluorescence response change.

7. The method of claim 2, wherein said generating includes using derivatives of said fluorescence response change and said light backscatter response change.

8. The method of claim 1, wherein said measuring occurs at pre-determined time intervals.

9. The method of claim 1, wherein said measuring includes using a front face fluorescence sensor including an ultraviolet light emitting diode with a peak intensity at about 280 nm directing light towards a fluorescent compound.

10. The method of claim 9, wherein said measured fluorescence change includes a waveband containing the fluorescence response of primarily tryptophan.

11. The method of claim 1, wherein said measured fluorescence change includes a waveband containing the fluorescence response of primarily riboflavin.

12. The method of claim 10, wherein said measuring includes centering said waveband at about 350 nm.

13. A method of deriving a cutting time prediction equation of a milk coagulum, comprising:

applying an ultraviolet light with a peak intensity of about 280 nm to the milk coagulum;

filtering reflected light from the milk coagulum through to a detector with both a high pass filter to remove light below 300 nm and a low pass filter to remove light above 475 nm to measure a fluorescence response;

developing a coagulation profile of milk using the fluorescence response of a compound within said milk coagulum;

analyzing said coagulation profile to determine said time parameter;

recording the endpoint selected by the cheese plant operator; and deriving said cutting time prediction equation using said time parameters and endpoint selected by the cheese plant operator.

14. The method of claim 13, wherein said analyzing includes regression analysis.

15. The method of claim 13, wherein said cutting time prediction equation is independent of the time at which an enzyme is added to said milk sample.

16. The method of claim 13, wherein said deriving includes using a first and second derivative of said fluorescence response.

17. The method of claim 13, wherein said cutting time prediction equation is dependent upon a time delay.

18. The method of claim 16, wherein said time delay is about 3 minutes.

19. The method of claim 13, wherein said cutting time prediction equation is dependent upon a product characteristic of said coagulating milk sample.

20. The method of claim 19, wherein said product characteristic is selected from a group consisting of fat, protein, solids content, sugar content, pH, temperature, enzyme type, and mixtures thereof.

* * * * *